(12) United States Patent
Zubok et al.

(10) Patent No.: US 7,357,038 B2
(45) Date of Patent: Apr. 15, 2008

(54) JOINT SIMULATOR TESTING MACHINE

(75) Inventors: Rafail Zubok, Midland Park, NJ (US); Joseph P. Errico, Green Brook, NJ (US); Michael W. Dudasik, Nutley, NJ (US)

(73) Assignee: SpineCore, Inc., Summit, NJ (US)

( * ) Notice: Subject to any disclaimer, the term of this patent is extended or adjusted under 35 U.S.C. 154(b) by 0 days.

(21) Appl. No.: 11/900,254

(22) Filed: Sep. 10, 2007

(65) Prior Publication Data

US 2008/0000305 A1 Jan. 3, 2008

Related U.S. Application Data

(63) Continuation of application No. 11/504,240, filed on Aug. 14, 2006, now Pat. No. 7,284,446, which is a continuation of application No. 11/334,000, filed on Jan. 18, 2006, now Pat. No. 7,131,338, which is a continuation of application No. 10/974,364, filed on Oct. 27, 2004, now Pat. No. 7,040,177, which is a continuation of application No. 10/384,981, filed on Mar. 10, 2003, now Pat. No. 6,865,954.

(51) Int. Cl.
*G01N 19/00* (2006.01)
(52) U.S. Cl. ..................................... 73/804
(58) Field of Classification Search ............... 73/804; 623/16.11–23.63, 914
See application file for complete search history.

(56) References Cited

U.S. PATENT DOCUMENTS

| | | | |
|---|---|---|---|
| 4,501,139 A | 2/1985 | Petersen | |
| 5,000,723 A | 3/1991 | Livingstone | |
| 5,030,238 A | 7/1991 | Neider et al. | |
| 5,049,797 A | 9/1991 | Phillips | |
| 5,078,650 A | 1/1992 | Foote | |
| 5,259,249 A | 11/1993 | Fetto | |
| 5,342,362 A | 8/1994 | Kenyon et al. | |
| 5,362,234 A | 11/1994 | Salazar et al. | |
| 6,058,784 A | 5/2000 | Carroll et al. | |
| 6,096,084 A | 8/2000 | Townley | |
| 6,244,943 B1 | 6/2001 | Bohler et al. | |
| 6,491,273 B2 | 12/2002 | King et al. | |
| 6,554,837 B1 | 4/2003 | Hauri et al. | |
| 6,602,042 B2 | 8/2003 | Roy et al. | |

(Continued)

OTHER PUBLICATIONS

U.S. Appl. No. 10/256,160, filed Sep. 26, 2002, entitled . . . "Artificial Intervertebral Disc Having Limited Rotation Using a Captured Ball and Socket Joint With a Solid Ball and Compression Locking Post".
www.enduratec.com, 'SmartTest® Servopneumatic Series', Higher Versatility Very Low Maintenance Unmatched Affordability, 4 pages.
www.enduratec.com, '4-Specimen Spinal Disk Wear Simulator', 3 pages.

(Continued)

*Primary Examiner*—Michael Cygan
*Assistant Examiner*—Octavia Davis
(74) *Attorney, Agent, or Firm*—Lerner, David, Littenberg, Krumholz & Mentlik, LLP

(57) ABSTRACT

A testing apparatus for a joint includes a support structure for engaging a first part a joint, an adapter for engaging a second part of the joint, a load assembly coupled with the adapter for applying a load onto the adapter and a drive assembly coupled with the adapter. Operation of the drive assembly causes angulation and rotation of the adapter relative to the support structure, which in turn causes angulation and rotation of the first and second parts of the joint relative to one another.

18 Claims, 8 Drawing Sheets

U.S. PATENT DOCUMENTS

| | | |
|---|---|---|
| 6,865,954 B2 | 3/2005 | Zubok et al. |
| 7,040,177 B2 | 5/2006 | Zubok et al. |
| 7,131,338 B2 | 11/2006 | Zubok et al. |
| 7,219,555 B2 * | 5/2007 | Salvesen ..................... 73/788 |
| 2002/0170361 A1 | 11/2002 | Vilendrer et al. |
| 2003/0040802 A1 | 2/2003 | Errico et al. |

OTHER PUBLICATIONS www.enduratec.com, Spinal Disk Fatigue/Wear Simulator (4-specimen/4-DOF). 4 pages.

www.enduratec.com, Drawings, Feb. 2003, archive.org, 1 page.

* cited by examiner

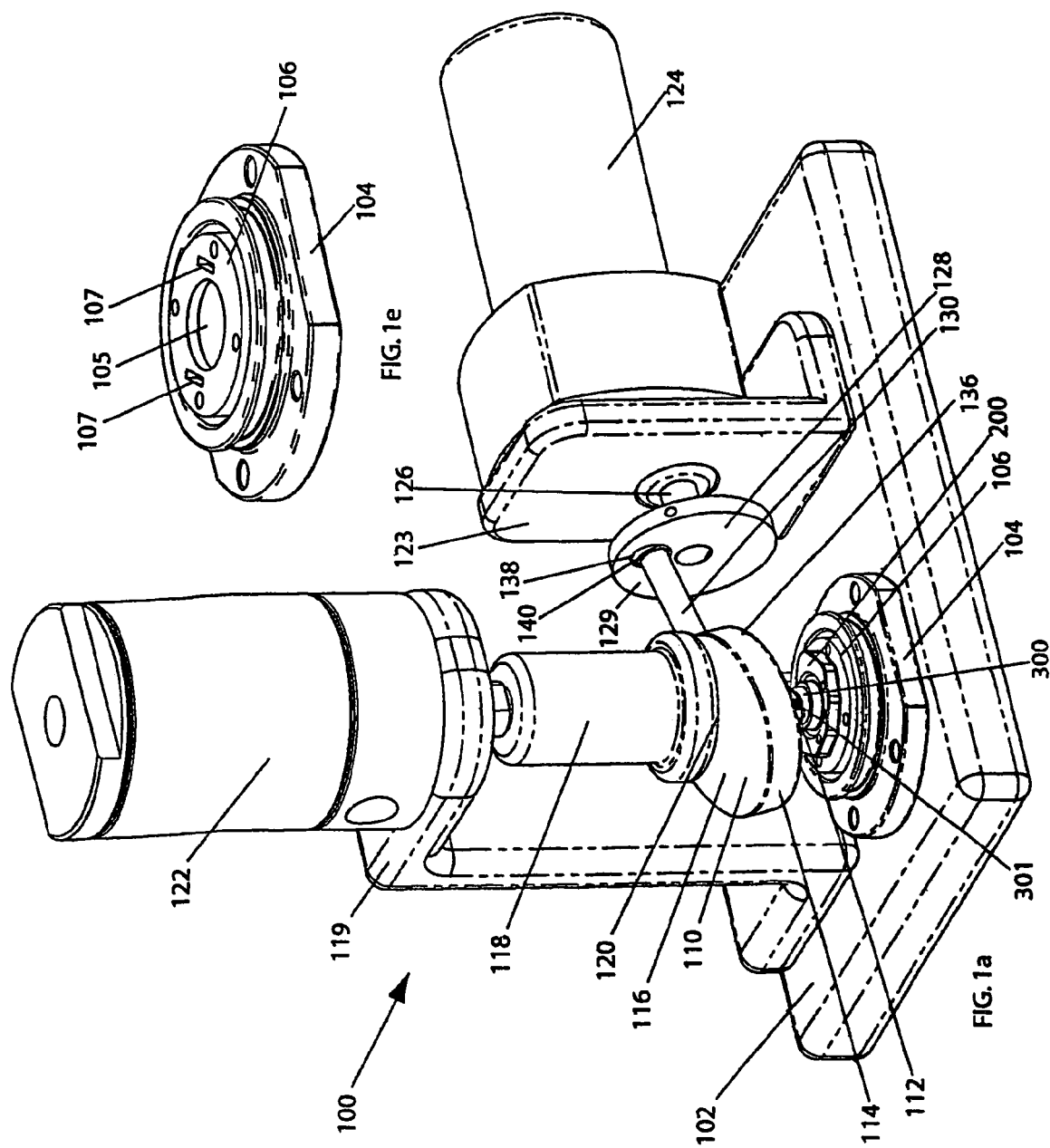

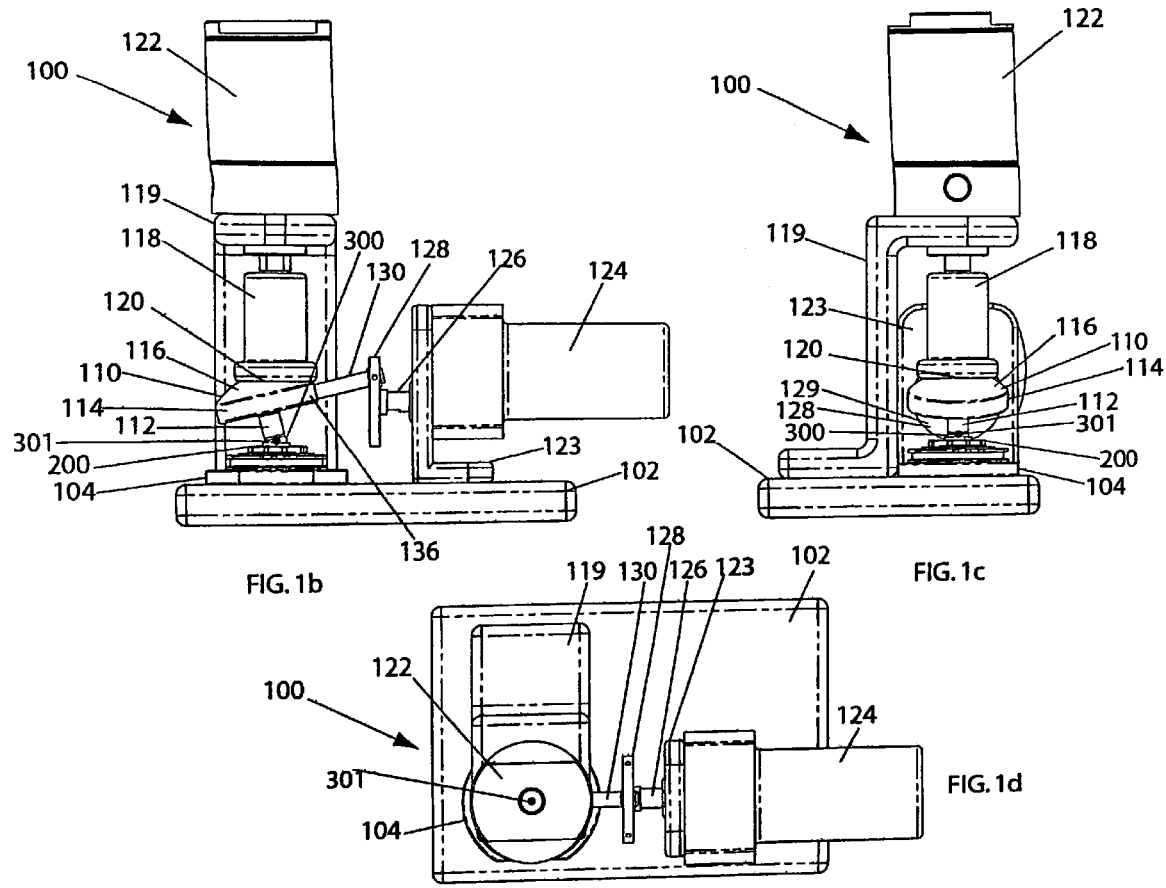

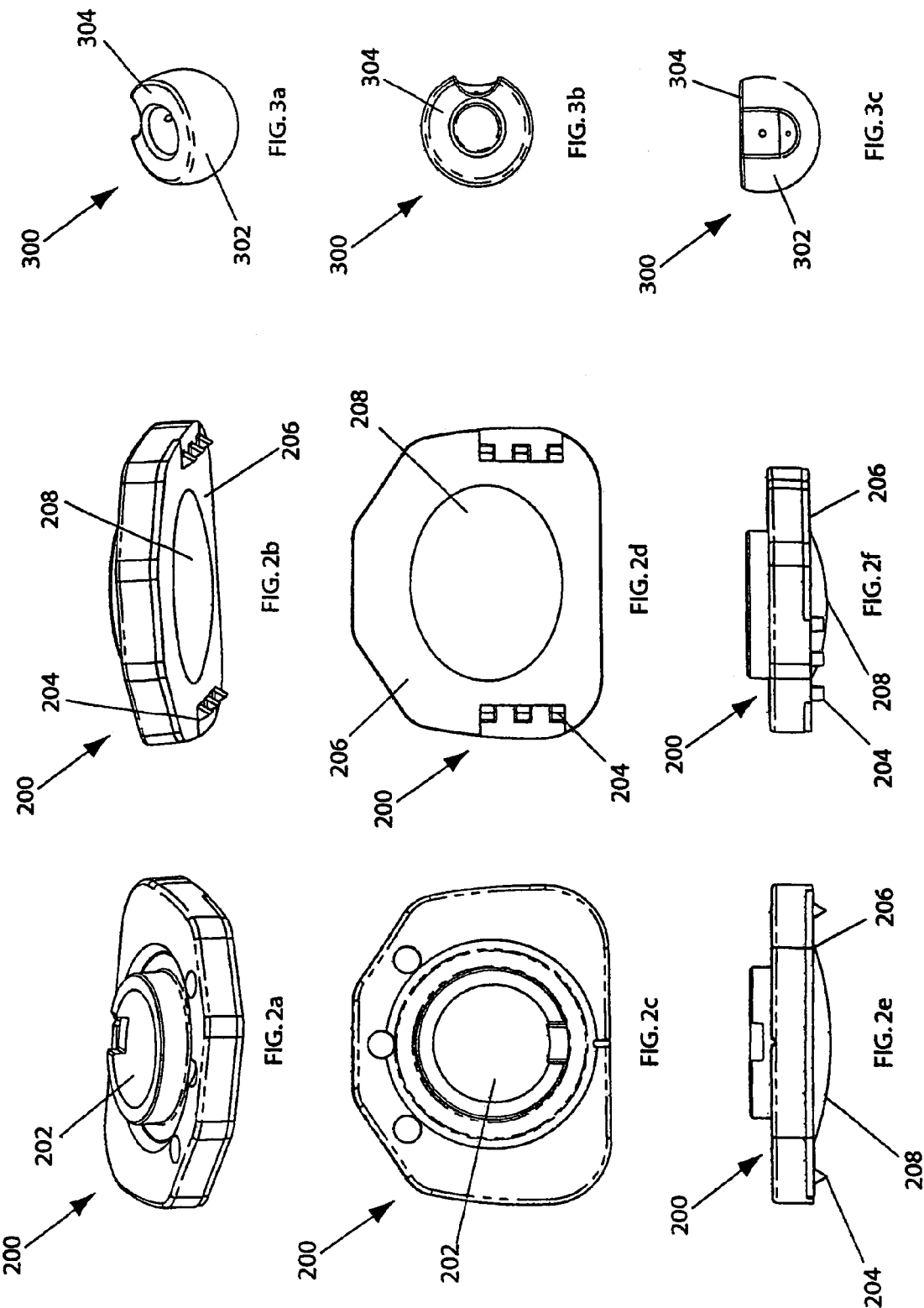

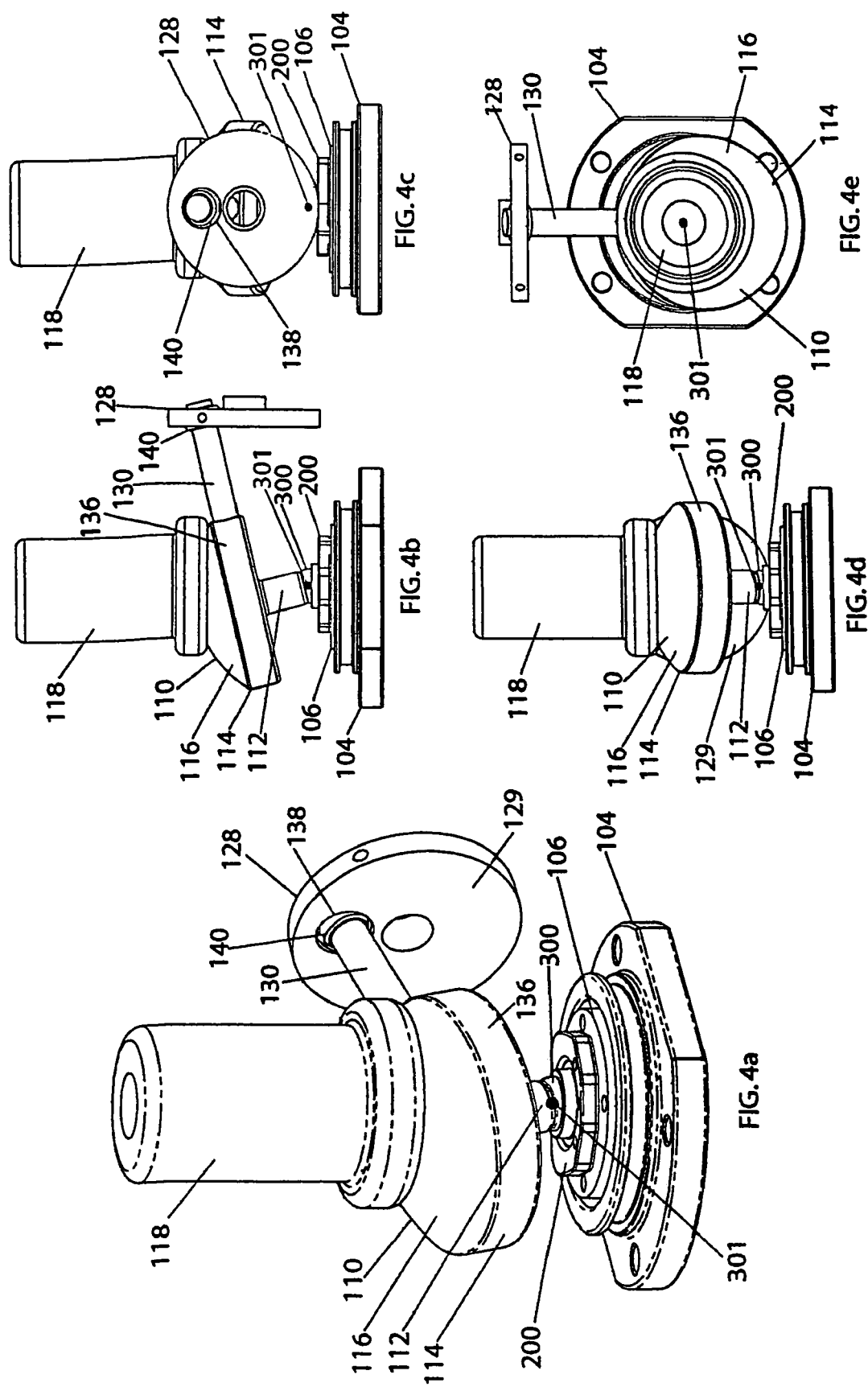

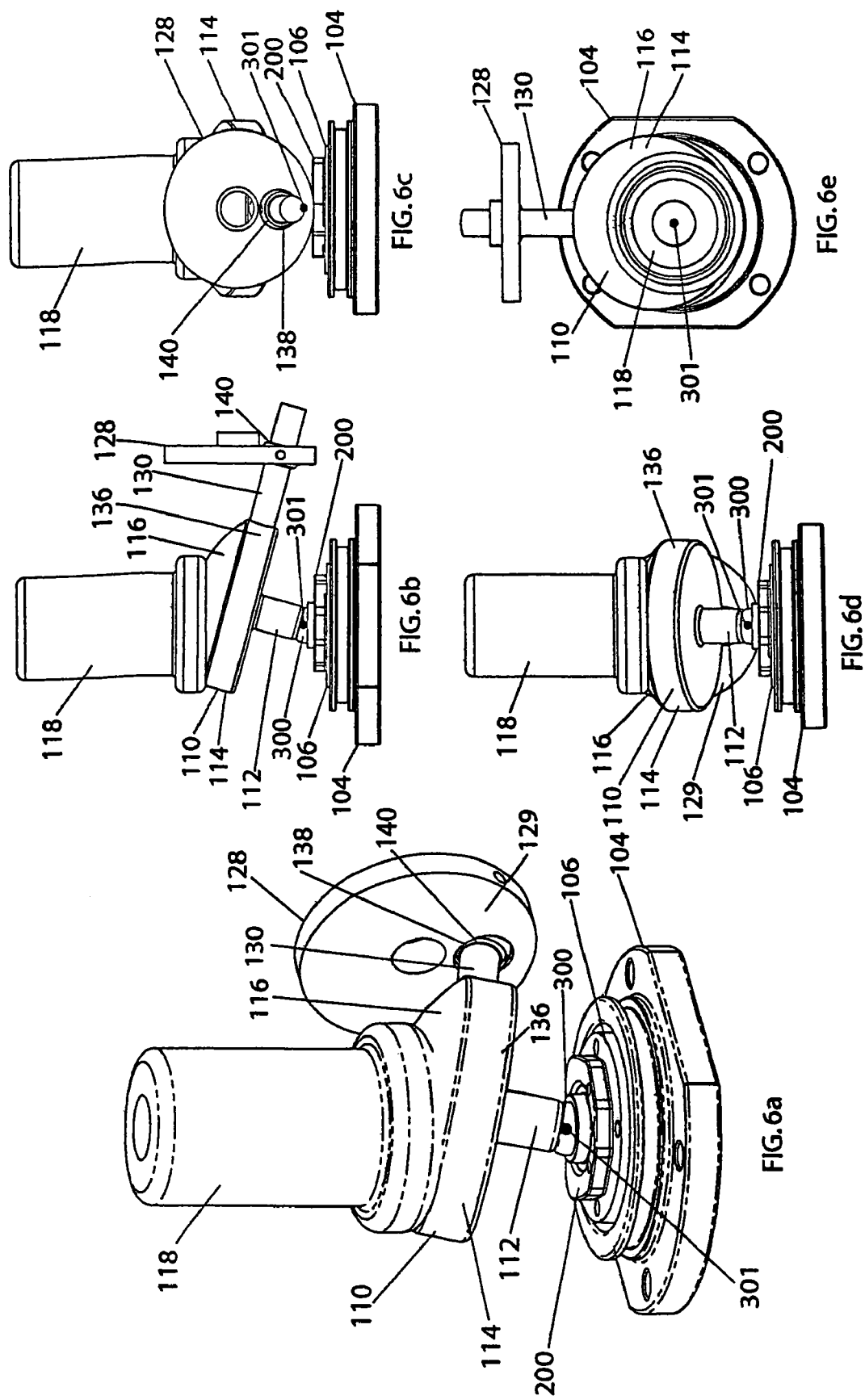

JOINT SIMULATOR TESTING MACHINE

CROSS REFERENCE TO RELATED APPLICATIONS

The present application is a continuation of U.S. application Ser. No. 11/334,000, filed Jan. 18, 2006, now U.S. Pat. No. 7,131,338, which is a continuation of U.S. application Ser. No. 10/974,364, filed Oct. 27, 2004, now U.S. Pat. No. 7,040,177, which is a continuation of U.S. application Ser. No. 10/384,981, filed Mar. 10, 2003, now U.S. Pat. No. 6,865,954, the disclosures of which are hereby incorporated by reference herein.

BACKGROUND OF THE INVENTION

This invention relates generally to joint simulators for testing purposes, and more specifically to joint simulators for testing components of a joint in articulation relative to one another under a load.

Artificial or prosthetic devices for replacing defective joints in humans have been the subject of extensive research and development efforts for many years, especially with regard to hip and knee joints, and more recently with spinal joints. In the design of such devices, it is advisable to subject the components of each new design to static and dynamic testing. Such testing is necessary to ensure that a particular design does not fail prematurely. Thus, a need exists within the medical equipment industry to assess the endurance properties of components of joint replacements.

While machines suitable for testing artificial or prosthetic hip and knee joints are known and are available to provide a variety of loading and articulation combinations, such machines have a variety of shortcomings, including large size, significant cost (both of purchase and maintenance), and slow speed. Moreover, many joint testing devices have been developed specifically for use with hip and knee joints, and in that respect are unsuitable for use with the growing number of spinal implants. The need to retrofit or completely redesign such machines for use with spinal implants increases the cost, and in some cases, the size.

Some devices have addressed these shortcomings to some degree. Enduratec (Minnetonka, Minn.) manufactures a Spinal Disc Implant Wear Testing System as well as a Spinal Disc Implant Wear Testing System, the respective capabilities and features of which are summarized at http://www.enduratec.com/testapp.cfm/tid/29 and http://www.enduratec.com/testapp.cfm/tid/27, respectively. While utilizing newer technologies to increase speed and minimize size, these devices are nevertheless costly and complicated in function for many uses.

Therefore, it is an object of the invention to provide a joint simulator testing machine that efficiently effects articulation of joint components under a load. It is also an object of the invention to provide a joint simulator testing machine that provides easy adjustment of the articulation pattern. Other objects of the invention not explicitly stated will be set forth and will be more clearly understood in conjunction with the descriptions of the preferred embodiments disclosed hereafter.

SUMMARY OF THE INVENTION

The preceding objects are achieved by the invention, which includes, among other aspects, a testing apparatus primarily for use in evaluating performance characteristics of a joint, and more particularly for testing components of a joint in articulation relative to one another under a load. Joints suitable for being evaluated by the testing apparatus include, for example, natural or artificial hip, knee, and intervertebral disc joints. As one example of a use of the testing apparatus of the present invention, the testing apparatus is illustrated in use with components of an artificial intervertebral disc, and specifically, a ball and socket joint, including a lower baseplate and a ball. The lower baseplate includes a semispherical pocket and the ball has a corresponding semispherical surface or contour such that the ball is seatable in the pocket for rotation and angulation therein. The testing apparatus engages both the baseplate and the ball, and causes the ball to articulate under a load and relative to the baseplate in the pocket to simulate conditions under which the ball and socket joint is desired to perform.

More particularly, the testing apparatus includes a support structure including a testing block. A head adapter is positioned between a load assembly (discussed below) and the testing block. One or more components of the device to be tested (referred to herein as the "test device") are held between the testing block and the head adapter, and, as will be described below, are preferably compressed toward one another between the testing block and the head adapter under a load applied by the load assembly, and movement of the head adapter by a drive assembly (discussed below) causes the components to articulate against one another under the load.

At least one component of the test device is supported by the support structure. In the illustrated embodiment, a first component (e.g., the lower baseplate) of the test device is supported by the testing block. Further in the illustrated embodiment, a second component (e.g., the ball) of the test device is positioned against the first component (e.g., the lower baseplate). Typically, the first and second components are to be tested in articulation against one another. Preferably, the second component (e.g., movable component) of the joint is disposed against and within a pocket of the first component (e.g., stationary component), with the pocket closely accommodating the contour of the second component such that the second component is articulatable within the pocket. In the illustrated embodiment, the ball is positioned with its semispherical contour in the curvate pocket of the lower baseplate with the semispherical pocket closely accommodating the semispherical surface of the ball for articulation thereagainst about a center of rotation (represented by dot) at the center of the sphere defined by the ball's semispherical surface, e.g., so that the ball can rotate and angulate with respect to the lower baseplate in a desired manner.

The head adapter serves as an extension of the second component (e.g., the ball), in that loading of the head adapter in turn loads the second component, and an articulation of the head adapter effects an angularly and positionally (e.g., translation movement as opposed to angulation or rotation) equivalent articulation of the second component. Thus, the head adapter is positioned and configured to engage the second component (e.g., the ball) of the test device. In the illustrated embodiment, the head adapter includes a cap and a stem that extends downwardly from the cap and has a lower end coupled to an engagement surface, e.g., a flat upper surface, of the ball. Preferably, the longitudinal axis of the stem is aligned with the center of rotation of the ball. Also preferably, the stem and ball are fixed to one another in this configuration and/or coupled in this configuration so that relative rotation therebetween is prevented during operation of the testing machine as described below.

With regard to compressing the components of the test device toward one another between the testing block and the head adapter under a load, a load assembly is configured in load applying relation to the head adapter (and accordingly configured in load applying relation to the second component (e.g., the ball) through the head adapter). For example, in the illustrated embodiment, the load assembly includes an air compressor disposed to apply a compressive load against the head adapter. A load adapter attached to the air compressor has a lower surface that is positioned against an upper surface of the cap and, during testing, the load generated by the air compressor is applied through the load adapter and against the upper surface of the cap and directed toward the apex of the pocket of the baseplate. Accordingly, at least a portion of the compressive load is transmitted through the stem of the head adapter, and against the component of the device to be tested that sits against the head adapter. In the illustrated embodiment, the compressive load is applied to the ball through the stem, and the direction of loading is preferably aligned with the center of rotation at the center of the sphere defined by the spherical contour of the ball.

Typically, the components of the test device are to be tested in articulation against one another under the compressive load, and in such embodiments, the head adapter is manipulated to, and configured to, facilitate the desired articulation. For example, in the illustrated embodiment, the ball is to be tested in articulation in and against the pocket of the lower baseplate about the center of rotation of the ball, because this motion mimics the articulation that the ball will undergo after the artificial intervertebral disc (of which the ball and lower baseplate are components) is implanted. Accordingly, as will be described below, the head adapter in the illustrated embodiment is moved by the testing apparatus in one or more articulation patterns that cause the ball to articulate as desired in the pocket of the lower baseplate, and is configured to maintain the desired center of rotation at the center of the sphere defined by the semispherical contour of the ball during such motion. More particularly with regard to the configuration of the head adapter, in order to maintain the testing center of rotation at the center of the sphere defined by the spherical contour of the ball, the upper surface of the cap of the head adapter is convex, having a semispherical surface or contour that is concentric with the semispherical contour of the ball (and thus with the center of rotation of the ball). Correspondingly, the lower surface (which contacts the upper surface of the cap) of the load adapter of the air compressor is concave, preferably having a semispherical surface or contour that matches the contour of the upper surface of the cap. Thus, the lower surface of the load adapter forms a pocket within which the upper surface of the cap can articulate about the center of rotation. Therefore, during testing, the load generated by the air compressor is transmitted through the load adapter and against the convex upper surface of the cap, and at least a portion of the load is transmitted through the stem of the head adapter, and against the ball, and is aligned with the center of rotation. And, therefore, articulation of the head adapter as described below causes an angularly equivalent articulation of the ball (i.e., the head adapter-ball combination articulates as a unitary element) about the center of rotation under the at least a portion of the load.

With regard to movement of the head adapter causing the components of the test device to articulate against one another under the load, a drive assembly is configured in articulating driving relation with the head adapter (and accordingly configured in articulating driving relation with the ball through the head adapter). For example, in the illustrated embodiment, the drive assembly includes a motor disposed to apply forces that move the head adapter, which in turn move the ball. The driving of the drive assembly effects an articulation of the head adapter about the center of rotation, which in turn effects an articulation of the ball in the semispherical pocket of the baseplate about the center of rotation. (The articulations are effected under the loading of the load assembly if the loading assembly is applying a load.) More particularly, in the illustrated embodiment, as discussed below, the head adapter is caused to rock forward and backward in a tilt plane parallel to the Y-Z plane about the center of rotation of the ball, and to rotate about the longitudinal axis of the stem, which is aligned with the center of rotation. Preferably, the angle swept by the longitudinal axis of the stem in the tilt plane is approximately 20 degrees, and the amount of rotation of the stem about its longitudinal axis is approximately 20 degrees total (10 degrees in one direction, and 10 degrees in the opposite direction), although it should be understood that the dimensions of the testing apparatus components and their spatial relationships to one another can be adjusted to vary these angles to effect other desired articulation patterns.

More particularly in the illustrated embodiment, a rotatable wheel is coupled to the motor and has an outer region spaced from an axis of rotation of the wheel. For example, preferably, a first or primary drive shaft of the motor has a first end mechanically coupled to the motor and a second end fixed to a central portion or region (preferably, a center) of the wheel such that a longitudinal axis of the primary drive shaft (about which the primary drive shaft rotates) is collinear with the axis of rotation of the wheel and perpendicularly intersects the longitudinal axis of the load adapter of the air compressor. A second or secondary drive shaft has a first end coupled to the outer region of the wheel (and as such the first end of the second drive shaft is spaced from the center of the wheel), and a second end fixed to a rim of the head adapter. A longitudinal axis of the secondary drive shaft is angled with respect to the axis of rotation of the wheel (also in this embodiment the longitudinal axis of the primary drive shaft), i.e., is convergent with the axis of rotation of the wheel toward the head adapter.

Accordingly, the second drive shaft is mechanically coupled in angular offset relation to the first drive shaft, and more particularly, the longitudinal axis of the second drive shaft is mechanically coupled in angular offset relation to the longitudinal axis (axis of rotation) of the first drive shaft, and to the axis of rotation of the wheel. The magnitude of the angular offset determines the articulation pattern of the head adapter and thus the articulation pattern of the ball. For example, preferably, the angular offset (e.g., angle of convergence) between the longitudinal axis of the secondary drive shaft and the axis of rotation of the wheel (also in this embodiment the longitudinal axis of the primary drive shaft) is approximately 10 degrees, which causes the angle swept by the longitudinal axis of the stem in the tilt plane (during testing) to be approximately 20 degrees. In addition, as will be described below, the angular offset causes the stem during testing to sweep an angle of 20 degrees as it rotates about the longitudinal axis of the stem. Inasmuch as in this embodiment the lower end of the stem is preferably coupled to the ball so that they are immovable relative to one another, the angular offset of 10 degrees in turn causes the ball to angulate in a range of 20 degrees (with some variation as noted above) in the tilt plane during testing, and to rotate in a range of 20 degrees (with some variation as noted above)

as it rotates about a longitudinal axis of the ball that is collinear with the longitudinal axis of the stem.

More particularly with respect to the coupling of the first end of the secondary drive shaft to the outer region of the wheel, the coupling preferably comprises a bore and a bearing fixed in the bore, through which bearing the secondary drive shaft passes. The bore is preferably angled to accommodate the desired approximate angular offset relationship between the longitudinal axis of the secondary drive shaft and the rotation axis of the wheel. Also, for reasons described below, the second drive shaft is longitudinally translatably and longitudinally rotatably coupled to the outer region of the wheel. For example, in the illustrated embodiment, the bearing permits linear translation of the secondary drive shaft within the bore (i.e., along the longitudinal axis of the secondary drive shaft) and rotation of the secondary drive shaft (about the longitudinal axis of the secondary drive shaft) with respect to the bore.

Accordingly, with regard to the motor applying forces that move the head adapter in the illustrated embodiment, the motor drives the primary drive shaft to rotate it about the longitudinal axis of the primary drive shaft, thus causing the wheel to rotate about its rotation axis passing through its center. The interference between the sides of the bore and the first end of the secondary drive shaft thus pushes the first end of the secondary drive shaft along with the bore (with the secondary drive shaft rotating with respect to the bore about the longitudinal axis of the secondary drive shaft as necessary). The outer region of the wheel accordingly travels in a circular path around the rotation axis of the wheel. The movement of the first end of the secondary drive shaft correspondingly (being in fixed relation to the second end of the secondary drive shaft) moves the second end of the secondary drive shaft, which correspondingly (being in fixed relation to the rim of the head adapter) moves the head adapter.

As the secondary drive shaft moves through its possible positions on the circular path, the head adapter (and in this embodiment the ball as well, inasmuch as they are fixed to one another in the described concentric configuration) is caused to rock forward and backward in a tilt plane, that is parallel to the Y-Z plane, about the center of rotation of the ball, and simultaneously to rotate about the longitudinal axis of the stem, which is aligned with the center of rotation. Accordingly, in the illustrated embodiment, in which the longitudinal axis of the secondary drive shaft is angled approximately 10 degrees with respect to the rotation axis of the wheel, the stem sweeps through approximately 20 degrees of tilt angulation about the center of rotation (approximately 10 degrees backward and 10 degrees forward), and the head adapter twice rotates about the longitudinal axis of the stem approximately 20 degrees (10 degrees clockwise, then 20 degrees counterclockwise, and then 10 degrees clockwise again). It should be understood that manipulations of the head adapter effect the same manipulations on the second component (e.g., the ball) when they are fixed to one another in this concentric configuration. Thus, the ball has swept through approximately 20 degrees of tilt angulation in the tilt plane about the center of rotation (approximately 10 degrees backward and 10 degrees forward), and the ball has twice rotated, about a longitudinal axis of the ball that is collinear with the longitudinal axis of the stem, approximately 20 degrees (10 degrees clockwise, then 20 degrees counterclockwise, and then 10 degrees clockwise again).

While the articulation pattern of the ball has been described as angulation about the center of rotation in a tilt plane parallel to the Y-Z plane during rotation about a longitudinal axis of the ball that remains in the tilt plane (as that longitudinal axis angulates in the tilt plane with the ball during the angulation of the ball), it should be understood that the angulation of the articulation can alternatively be described as being in two planes that are, for example, perpendicular to one another and intersect with one another at a line of intersection that extends in the Z direction and is perpendicular to the axis of rotation of the wheel. Therefore, the articulation pattern would include angulation about the center of rotation in a first plane (e.g., a first of those planes), during angulation about the center of rotation in a second plane (e.g., a second of those planes), during rotation about a longitudinal axis of the second component (e.g., the ball) that remains in a third plane that intersects the first and second planes at a line of intersection that is perpendicular to the axis of rotation of the wheel (e.g., the third plane can be the above described tilt plane that is parallel to the Y-Z plane and include the axis of rotation of the wheel). It should be understood that these examples of alternate geometric frameworks are provided to illustrate the utility of the invention to enable measurement of the joint performance, and/or ensure sufficient angulation and/or rotation of the joint components, in multiple planes and axes using appropriate mathematical equations to quantify the relationship of the angulations and rotations relative to the rotation axis of the wheel and the other geometric reference points discussed, and that other geometric frameworks can be referenced as necessary to achieve desired performance, measurements, or evaluations.

BRIEF DESCRIPTION OF THE DRAWINGS

FIGS. 1a-d show a testing apparatus of the present invention in perspective, front, side, and top views, respectively.

FIG. 1e shows a magnified view of a testing support block and testing block of the testing apparatus of FIGS. 1a-d.

FIGS. 2a-f show a baseplate component of a test device suitable for being tested by the testing apparatus of FIGS. 1a-d, in top perspective, bottom perspective, top, bottom, front, and side views, respectively.

FIGS. 3a-c show a ball component of a test device suitable for being tested by the testing apparatus of FIGS. 1a-d, in perspective, top, and side views, respectively.

FIGS. 4a-e show certain elements of the testing apparatus of FIGS. 1a-d with a first end of a secondary drive shaft of the testing apparatus at a top position, in perspective, front, right side, left side, and top views, respectively.

FIGS. 6a-e show certain elements of the testing apparatus of FIGS. 1a-d with a first end of a secondary drive shaft of the testing apparatus at a bottom position, in perspective, front, right side, left side, and top views, respectively.

DETAILED DESCRIPTION

Figure 5A:
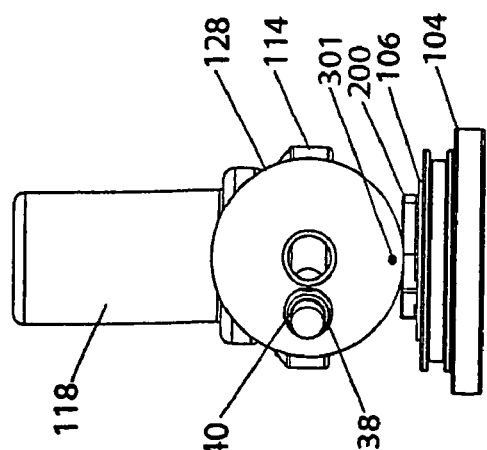
FIGS. 5a-e show certain elements of the testing apparatus of FIGS. 1a-d with a first end of a secondary drive shaft of the testing apparatus at a right position, in perspective, front, right side, left side, and top views, respectively.
Figure 5B:
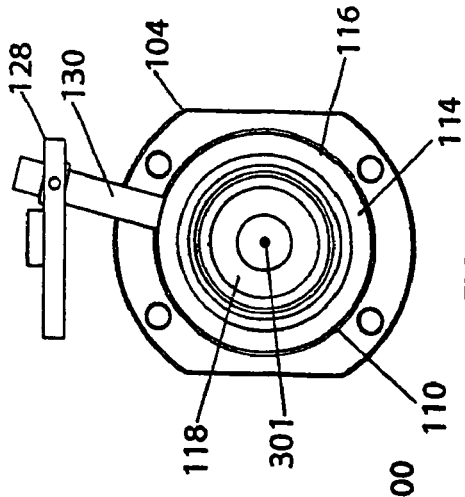
Figure 5C:
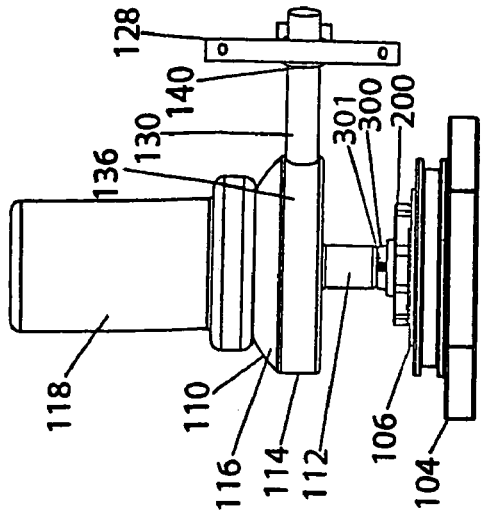
Figure 5D:
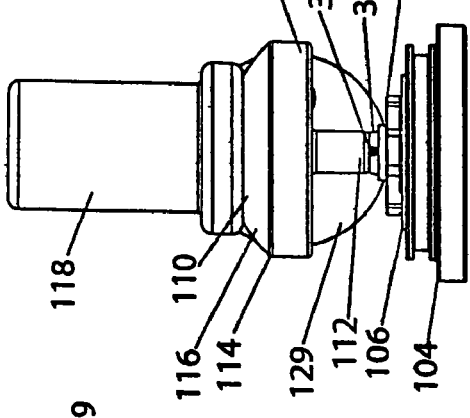
Figure 5E:
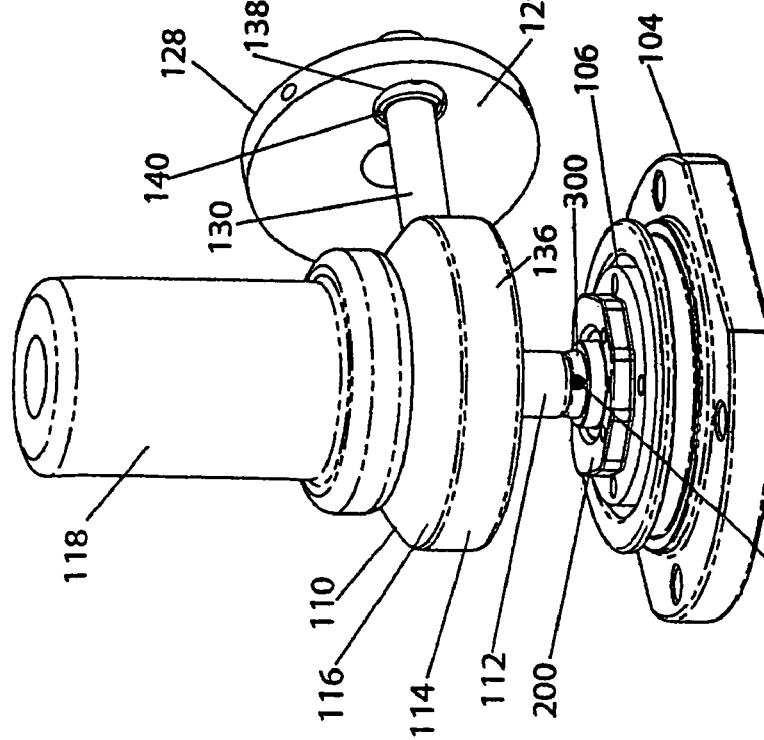
Figure 7C:
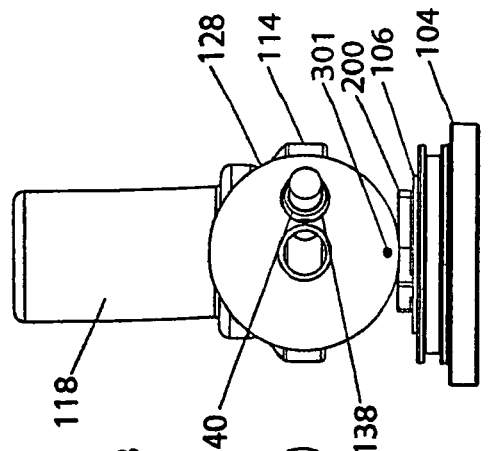
FIGS. 7a-e show certain elements of the testing apparatus of FIGS. 1a-d with a first end of a secondary drive shaft of the testing apparatus at a left position, in perspective, front, right side, left side, and top views, respectively.
Figure 7E:
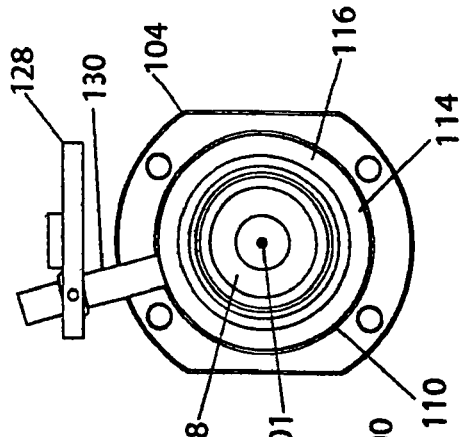
Figure 7B:
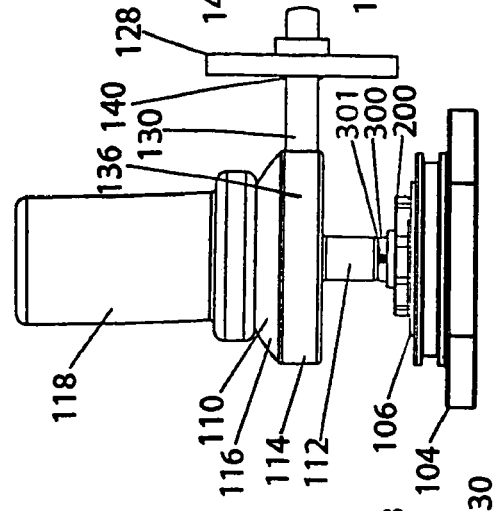
Figure 7D:
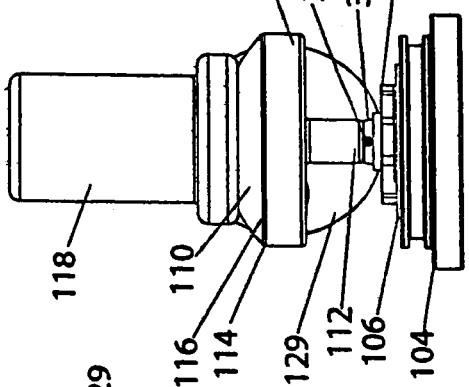
Figure 7A:
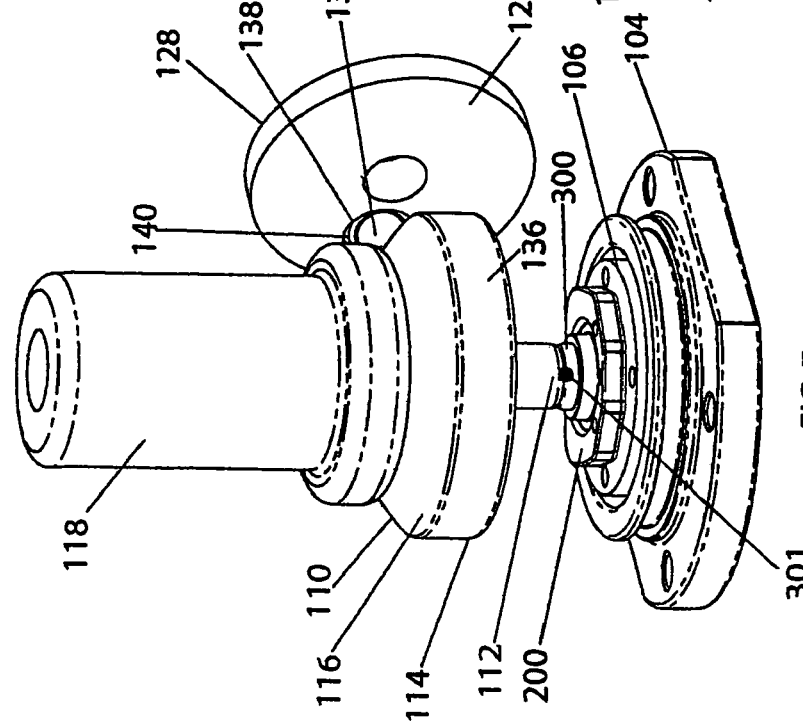

While the invention will be described more fully hereinafter with reference to the accompanying drawings, it is to be understood at the outset that persons skilled in the art may modify the invention herein described while achieving the functions and results of the invention. Accordingly, the descriptions that follow are to be understood as illustrative and exemplary of specific structures, aspects and features within the broad scope of the invention and not as limiting of such broad scope. Like numbers refer to similar features of like elements throughout.

Referring now to FIGS. 1a-d, a preferred embodiment of a testing apparatus of the present invention is shown in perspective, front, side, and top views, respectively. The illustrated testing apparatus 100 is provided primarily for use in evaluating performance characteristics of a joint, and more particularly for testing components of a joint in articulation relative to one another under a load. Joints suitable for being evaluated by the testing apparatus include, for example, natural or artificial hip, knee, and intervertebral disc joints. As one example of a use of the testing apparatus of the present invention, the testing apparatus 100 is illustrated in use with components of an artificial intervertebral disc, and specifically, a ball and socket joint, including a lower baseplate 200 (shown in top perspective, bottom perspective, top, bottom, front, and side views in FIGS. 2a-f, respectively) and a ball 300 (shown in perspective, top, and side views in FIGS. 3a-c, respectively) of the artificial intervertebral disc illustrated in U.S. patent application Ser. No. 10/256,160 (filed Sep. 26, 2002) entitled "Artificial Intervertebral Disc Having Limited Rotation Using a Captured Ball and Socket Joint With a Solid Ball and Compression Locking Post" (hereinafter referred to as "the '160 application"), which is hereby incorporated by reference herein in its entirety. As discussed in greater detail in the '160 application, and as shown in FIGS. 2a-f and 3a-c, the lower baseplate 200 includes a semispherical pocket 202 and the ball 300 has a corresponding semispherical surface or contour 302 such that the ball 300 is seatable in the pocket 202 for rotation and angulation therein. The testing apparatus 100 engages both the baseplate 200 and the ball 300, and causes the ball 300 to articulate under a load and relative to the baseplate 200 in the pocket 202 to simulate conditions under which the ball and socket joint is desired to perform.

For purposes of explanation only, and without limiting the structure of the present invention, the elements of the illustrated testing apparatus are discussed with reference to an X direction, a Y direction perpendicular to the X direction, and a Z direction perpendicular to the X direction and perpendicular to the Y direction (referred to herein as an "X-Y-Z reference frame"). Accordingly, an X-Y plane is defined as the plane extending in the X direction and the Y direction, and which extends perpendicular to the Z direction. And, accordingly, a Y-Z plane is defined as the plane extending in the Y direction and the Z direction, and which extends perpendicular to the X direction. And, accordingly, an X-Z plane is defined as the plane extending in the X direction and the Z direction, and which extends perpendicular to the Y direction.

More particularly, as shown in FIGS. 1a-d, the testing apparatus 100 includes a support structure including, for example, a support plate 102 that extends parallel to the X-Y plane and has a thickness in the Z direction, a support block 104 mounted on the support plate 102, and a testing block 106 mounted on the support block 104. An adapter, or head adapter 110, is positioned between a load assembly (discussed below) and the testing block 106 (in the illustrated embodiment, the head adapter 110 is positioned above the testing block 106). One or more components of the device to be tested (referred to herein as the "test device") are held between the testing block 106 and the head adapter 110, and, as will be described below, are preferably compressed toward one another between the testing block 106 and the head adapter 110 under a load applied by the load assembly, and movement of the head adapter 110 by a drive assembly (discussed below) causes the components to articulate against one another under the load.

Accordingly, at least one component of the test device is supported by the support structure, particularly in the illustrated embodiment by the testing block 106. In the illustrated embodiment, a first component (e.g., the lower baseplate 200) of the test device is supported by the testing block 106. For example, as illustrated in FIG. 1e (which shows a magnified view of the testing block 106 on the support block 104), and referring again to FIGS. 2a-f, the upper surface 108 of the testing block 106 is shaped to accommodate the lower surface 206 of the lower baseplate 200 so that the lower baseplate 200 is maintained in a desired position on the testing block 106 during the testing process. For example, as discussed in greater detail in the '160 application, the lower baseplate 200 of the artificial intervertebral disc has a convex dome 208 and a plurality of spikes 204 for engagement with a vertebral body when the artificial disc is implanted into an intervertebral space. Accordingly, in this example, the upper surface 108 of the testing block 106 is shaped to receive the convex dome 208 and the spikes 204 when the lower baseplate 200 is placed thereon. More particularly, the upper surface 108 has a central recess 105 having a perimeter larger than that of the convex dome 208, and recesses 107 dimensioned to accept the spikes 204; this helps maintain the lower baseplate 200 on the testing block 106 during the testing process. Preferably, the testing block 106 is formed from polyethylene.

Further in the illustrated embodiment, and referring again to FIGS. 3a-c, a second component (e.g., the ball 300) of the test device is positioned against the first component (e.g., the lower baseplate 200). Typically, the first and second components are to be tested in articulation against one another. (It should be understood that although the testing apparatus of the present invention is illustrated and discussed with regard to testing two device components that articulate against one another under a load, the testing apparatus of the present invention can be adapted within the scope of the present invention to test one component articulating and/or loaded against a testing block, or to test more than one component articulating and/or loaded against a testing block and/or one or more other components.) Preferably, the second component (e.g., movable component) of the joint is disposed against and within a pocket of the first component (e.g., stationary component), with the pocket closely accommodating the contour of the second component such that the second component is articulatable within the pocket. In the illustrated embodiment, the ball 300 is positioned with its semispherical contour 302 in the curvate pocket 202 of the lower baseplate 200 with the semispherical pocket 202 closely accommodating the semispherical surface 302 of the ball 300 for articulation thereagainst about a center of rotation (represented by dot 301) at the center of the sphere defined by the ball's semispherical surface 302, e.g., so that the ball 300 can rotate and angulate with respect to the lower baseplate 200 in a desired manner.

The head adapter (e.g., 110) serves as an extension of the second component (e.g., the ball 300), in that loading of the head adapter 110 in turn loads the second component, and an articulation of the head adapter 110 effects an angularly and positionally (e.g., translation movement as opposed to angulation or rotation) equivalent articulation of the second component. Thus, the head adapter (e.g., 110) is positioned and configured to engage the second component (e.g., the ball 300) of the test device. In the illustrated embodiment, the head adapter 110 includes a cap 114 and a stem 112 that extends downwardly (e.g., depends centrally) from the cap 114 and has a lower end coupled to an engagement surface, e.g., a flat upper surface 304, of the ball 300. Preferably, the longitudinal axis of the stem 112 is aligned with the center of rotation 301. Also preferably, the stem 112 and ball 300 are fixed to one another in this configuration and/or coupled in this configuration so that relative rotation therebetween is prevented (e.g., by the ball 300 having a slot (not shown) into which a corresponding key (not shown) on the stem 112 fits) during operation of the testing machine 100 as described below. It should be understood that while the stem 112 is shown as cylindrical, it can take any other suitable shape (e.g., tapered and/or curvate sides) without departing from the scope of the present invention. It should also be understood that while the illustrated embodiment functions such that the ball 300 undergoes angularly and positionally equivalent articulations as those of the head adapter 110, embodiments having head adapters that are shaped, dynamically altered, or otherwise configured to provide positionally equivalent or positionally non-equivalent, and/or angularly equivalent or angularly non-equivalent (but preferably predictable) movements are also contemplated by the present invention. That is, in some embodiments, an articulation of the head adapter effects an articulation of the second component (e.g., the ball 300) that differs from the articulation of the head adapter because the head adapter is, e.g., shaped or dynamically altered during testing to exaggerate, multiply, enhance, diminish, decrease, vary, make random, or otherwise adjust the articulation parameters of the second component to differ from the articulation of the head adapter.

With regard to compressing the components of the test device toward one another between the testing block 106 and the head adapter 110 under a load, a load assembly is configured in load applying relation to the head adapter (e.g., 110) (and accordingly configured in load applying relation to the second component (e.g., the ball 300) through the head adapter). For example, in the illustrated embodiment, the load assembly includes a compression load applying device, or compression loader, e.g., an air compressor 122, disposed to apply a compressive load against the head adapter 110. More particularly, a first mounting bracket 119 is fixed to the support plate 102 and supports the air compressor 122. A load adapter 118 attached to the air compressor 122 has a longitudinal axis aligned with the apex of the pocket 202 of the lower baseplate 200 when the lower baseplate 200 is supported on the testing block 106. The load adapter 118 further has a lower surface 120 that is positioned against an upper surface 116 of the cap 114 and, during testing, the load generated by the air compressor 122 is applied through the load adapter 118 and against the upper surface 116 of the cap 114 and directed toward the apex of the pocket 202 of the baseplate 200 (the direction of loading being collinear with a plane parallel to the Y-Z plane). (It should be understood that the loading can be applied in other directions, and/or multiple loads from one or more directions can be applied, without departing from the scope of the invention. Further, it should be understood that although the illustrated embodiment discloses testing components of a joint in compression against one another, embodiments testing components of a joint under tension loading are also contemplated by the present invention.) Accordingly, at least a portion of the compressive load (the portion being dictated by the angle at which the longitudinal axis of the stem 112 is angularly misaligned with respect to the longitudinal axis of the load adapter 118 at a given articulated position of the head adapter 110 during testing) is transmitted through the stem 112 of the head adapter 110, and against the component of the device to be tested that sits against the head adapter 110.

In the illustrated embodiment, the compressive load is applied to the ball 300 through the stem 112, and the direction of loading is preferably aligned with the center of rotation (represented by dot 301) at the center of the sphere defined by the spherical contour 302 of the ball 300. It should be understood that embodiments in which the direction of loading is not aligned with the center of rotation of the second component are also contemplated by the present invention.

Typically, the components of the test device are to be tested in articulation against one another under the compressive load, and in such embodiments, the head adapter 110 is manipulated to, and configured to, facilitate the desired articulation. For example, in the illustrated embodiment, the ball 300 is to be tested in articulation in and against the pocket 202 of the lower baseplate 200 about the center of rotation 301, because this motion mimics the articulation that the ball 300 will undergo after the artificial intervertebral disc (of which the ball 300 and lower baseplate 200 are components) is implanted. Accordingly, as will be described below, the head adapter 110 in the illustrated embodiment is moved by the testing apparatus 100 in one or more motion patterns that cause the ball 300 to articulate as desired in the pocket 202 of the lower baseplate 200, and is configured to maintain the desired center of rotation 301 at the center of the sphere defined by the semispherical contour 302 of the ball 300 during such motion. More particularly with regard to the configuration of the head adapter 110, in order to maintain the testing center of rotation 301 at the center of the sphere defined by the spherical contour 302 of the ball 300, the upper surface 116 of the cap 114 of the head adapter 100 is convex, having a semispherical surface or contour that is concentric with the semispherical contour 302 of the ball 300 (and thus with the center of rotation 301). Correspondingly, the lower surface 120 (which contacts the upper surface 116 of the cap 114) of the load adapter 118 of the air compressor 122 is concave, preferably having a semispherical surface or contour that matches the contour of the upper surface 116 of the cap 114. Thus, the lower surface 120 of the load adapter 118 forms a pocket within which the upper surface 116 of the cap 114 can articulate about the center of rotation 301. Therefore, during testing, the load generated by the air compressor 122 is transmitted through the load adapter 118 and against the convex upper surface 116 of the cap 114, and at least a portion of the load is transmitted through the stem 112 of the head adapter 110, and against the ball 300, and is aligned with the center of rotation 301. And, therefore, articulation of the head adapter 110 as described below causes an angularly equivalent articulation of the ball 300 (i.e., the head adapter 110-ball 300 combination articulates as a unitary element) about the center of rotation 301 under the at least a portion of the load (the portion being dictated by the angle at which the longitudinal axis of the stem 112 is angularly misaligned with respect to the longitudinal axis of the load adapter 118 at a given articulated position of the head adapter 110 during testing). It should be noted that while the lower surface 120 preferably has a contour matching that of upper surface 116, it is not necessary for proper operation of the testing apparatus 100, so long as the desired movements described herein are possible. For example, the lower surface 120 need not be flush against the upper surface 116 (causing continuous surface-to-surface contact during testing), but rather, e.g., the lower surface 120 could have a contour that is more concave than that of the upper surface 116 (or, e.g., be a cylindrical recess), resulting in a circle of contact, rather than an area of contact, between the upper surface 116 and the head adapter 110 without departing from the scope of the present invention. It should be understood that in some embodiments of the present invention, a head adapter element may not be necessary, in that, e.g., the second component may be couplable directly to a drive assembly of the present invention (described below), and that in embodiments employing a head adapter element, the element need not be shaped as described herein, but rather can have any shape or configuration that effects desired movement of the second component and/or serves as a manipulatable extension of the second component to enable manipulation of the second component.

With regard to movement of the head adapter 110 causing the components of the test device to articulate against one another under the load, a drive assembly is configured in articulating driving relation with the head adapter 110 (and accordingly configured in articulating driving relation with the ball 300 through the head adapter 110). For example, in the illustrated embodiment, the drive assembly includes a motion applying device, e.g., a motor 124, disposed to apply forces that move the head adapter 110, which in turn move the ball 300. In some embodiments, motion control structures (e.g., panels, flanges, protuberances, or the like), are disposed on the head adapter 110, on the support plate 102, and/or supported elsewhere on the testing apparatus 110, to prevent undesirable movement of the head adapter 110, so that the head adapter 110 moves in a desired manner to effect the desired movement of the device components to be tested.

The driving of the drive assembly effects an articulation of the head adapter 110 about the center of rotation 301, which in turn effects an articulation of the ball 300 in the semispherical pocket 202 of the baseplate 200 about the center of rotation 301. (The articulations are effected under the loading of the load assembly if the loading assembly is applying a load.) (It should be understood that while the illustrated embodiment functions such that the ball 300 undergoes angularly equivalent articulations as those of the head adapter 110, embodiments having head adapters that are shaped or dynamically altered or otherwise configured to provide positionally equivalent or positionally non-equivalent, and/or angularly equivalent or angularly non-equivalent (but preferably predictable) movements are also contemplated by the present invention.) More particularly, in the illustrated embodiment, as discussed below, the head adapter 110 is caused to rock forward and backward in a tilt plane parallel to the Y-Z plane about the center of rotation 301, and to rotate about the longitudinal axis of the stem 112, which is aligned with the center of rotation 301. Preferably, the angle swept by the longitudinal axis of the stem 112 in the tilt plane is approximately 20 degrees, and the amount of rotation of the stem 112 about its longitudinal axis is approximately 20 degrees total (10 degrees in one direction, and 10 degrees in the opposite direction), although it should be understood that the dimensions of the testing apparatus components and their spatial relationships to one another can be adjusted to vary these angles to effect other desired articulation patterns.

More particularly in the illustrated embodiment, a second mounting bracket 123 is fixed to the support plate 102 and supports the motor 124. A rotatable wheel 128 is coupled to the motor 124 and has an outer region spaced from an axis of rotation of the wheel 128. For example, preferably, a first or primary drive shaft 126 of the motor 124 has a first end mechanically coupled to the motor 124 and a second end fixed to a central portion or region (preferably, a center) of the wheel 128 such that a longitudinal axis of the primary drive shaft 126 (about which the primary drive shaft 126 rotates) is collinear with the axis of rotation of the wheel 128 and perpendicularly intersects the longitudinal axis of the load adapter 118 of the air compressor 122. A second or secondary drive shaft 130 has a first end coupled to the outer region of the wheel 128 (and as such the first end of the second drive shaft 130 is spaced from the center of the wheel 128), and a second end fixed to a rim 136 of the head adapter 110. A longitudinal axis of the secondary drive shaft 130 is angled with respect to the axis of rotation of the wheel 128 (also in this embodiment the longitudinal axis of the primary drive shaft 126), i.e., is convergent with the axis of rotation of the wheel 128 toward the head adapter 110).

Accordingly, the second drive shaft 130 is mechanically coupled in angular offset relation to the first drive shaft, and more particularly, the longitudinal axis of the second drive shaft 130 is mechanically coupled in angular offset relation to the longitudinal axis (axis of rotation) of the first drive shaft, and to the axis of rotation of the wheel 128. (It should be understood that the present invention is not limited to any particular numbers, types, or configurations of drive shafts, wheels, or other driving elements or mechanisms, and that the angular offset relation between the axis of rotation and a controlling axis of the element (e.g., second drive shaft 130) connected between the rotating element (e.g., wheel 128) and the adapter element (e.g., head adapter 110), or the second component (e.g., the ball 300) directly, can be established in any other suitable manner without departing from the scope of the present invention). The magnitude of the angular offset determines the articulation pattern of the head adapter 110 and thus the articulation pattern of the ball 300. For example, preferably, the angular offset (e.g., angle of convergence) between the longitudinal axis of the secondary drive shaft 130 and the axis of rotation of the wheel 128 (also in this embodiment the longitudinal axis of the primary drive shaft 126) is approximately 10 degrees, which causes the angle swept by the longitudinal axis of the stem 112 in the tilt plane (during testing) to be approximately 20 degrees (although in some embodiments the actual swept angle varies slightly from 20 degrees by an amount dictated by the spatial relationships of the components of the testing apparatus 100 during the testing procedure). As will be described below, the varying of the swept angle is accommodated by the clearances of the coupling of the first end of the secondary drive shaft 130 to the outer region of the wheel 128. In addition, as will be described below, the angular offset (e.g., angle of convergence) between the longitudinal axis of the secondary drive shaft 130 and the rotation axis of the wheel 128 (also in this embodiment the longitudinal axis of the primary drive shaft 126) of approximately 10 degrees causes the stem 112 during testing to sweep an angle of 20 degrees as it rotates about the longitudinal axis of the stem 112. Inasmuch as in this embodiment the lower end of the stem 112 is preferably coupled to the ball 300 so that they are immovable relative to one another, the angular offset of 10 degrees in turn causes the ball 300 to angulate in a range of 20 degrees (with some variation as noted above) in the tilt plane during testing, and to rotate in a range of 20 degrees (with some variation as noted above) as it rotates about a longitudinal axis of the ball 300 that is collinear with the longitudinal axis of the stem 112.

More particularly with respect to the coupling of the first end of the secondary drive shaft 130 to the outer region of the wheel 128, the coupling preferably comprises a bore 138 and a bearing 140 fixed in the bore 138, through which bearing 140 the secondary drive shaft 130 passes. The bore 138 is preferably angled to accommodate the desired approximate angular offset relationship between the longitudinal axis of the secondary drive shaft 130 and the rotation axis of the wheel 128 (also in this embodiment the longitudinal axis of the primary drive shaft 126). For example, if the longitudinal axis of the secondary drive shaft 130 is designed to be angled approximately 10 degrees with respect to the rotation axis of the wheel 128 during testing, the bore 138 is preferably formed at a 10 degree angle with respect to the rotation axis of the wheel 128. Therefore, the secondary drive shaft 130 fits through the bore 138 to couple the secondary drive shaft 130 to the wheel 128 at the desired angle. To accommodate the fact that the angle between the longitudinal axis of the secondary drive shaft 130 and the rotation axis of the wheel 128 varies slightly during operation of the testing apparatus 100 in some embodiments (dictated by the spatial relationships of the components of the testing apparatus 100), appropriate clearance is established between the secondary drive shaft 130 and the bearing 140, so that as the angle between the longitudinal axis of the secondary drive shaft 130 and the longitudinal axis of the bore 140 slightly varies during testing, the bore 140 will still accommodate the secondary drive shaft 130. Also, for reasons described below, the second drive shaft 130 is longitudinally translatably and longitudinally rotatably coupled to the outer region of the wheel 128. For example, in the illustrated embodiment, the bearing 140 permits linear translation of the secondary drive shaft 130 within the bore 140 (i.e., along the longitudinal axis of the secondary drive shaft 130) and rotation of the secondary drive shaft 130 (about the longitudinal axis of the secondary drive shaft 130) with respect to the bore 140.

Accordingly, with regard to the motor 124 applying forces that move the head adapter 110 in the illustrated embodiment, the motor 124 drives the primary drive shaft 126 to rotate it about the longitudinal axis of the primary drive shaft 126, thus causing the wheel 128 to rotate about its rotation axis passing through its center (e.g., in the clockwise direction when viewing the face 129 of the wheel 128). The interference between the sides of the bore 140 and the first end of the secondary drive shaft 130 thus pushes the first end of the secondary drive shaft 130 along with the bore 140 (with the secondary drive shaft 130 rotating with respect to the bore 140 about the longitudinal axis of the secondary drive shaft 130 as necessary). The outer region of the wheel 128 accordingly travels in a circular path around the rotation axis of the wheel 128 (also in this embodiment the longitudinal axis of the first drive shaft 128). The movement of the first end of the secondary drive shaft 130 correspondingly (being in fixed relation to the second end of the secondary drive shaft 130) moves the second end of the secondary drive shaft 130, which correspondingly (being in fixed relation to the rim 136 of the head adapter 110) moves the head adapter 110.

Referring now to FIGS. 4*a-e*, 5*a-e*, 6*a-e*, and 7*a-e*, for purposes of explanation, the motion of the head adapter 110 will be discussed with reference to four of the possible positions, along the circular path, of the first end of the secondary drive shaft 130 with respect to the rotation axis of the wheel 128 (also in this embodiment the longitudinal axis of the primary drive shaft 126) (with the understanding that the first end of the secondary drive shaft 130 moves smoothly and continuously from each position on the path to the next as the wheel 128 turns during the testing procedure). Referencing the positions of the first end of the secondary drive shaft 130 on the face 129 of the wheel 128 as corresponding to numbers on a clock for purposes of explanation only, a top position of the first end of the secondary drive shaft 130 (shown in FIGS. 4*a-e*) will be discussed as the position of the first end of the secondary drive shaft 130 when the bore 138 is at the twelve o'clock position on the face 129 of the wheel 128. And, a right position of the first end of the secondary drive shaft 130 (shown in FIGS. 5*a-e*) will be discussed as the position of the first end of the secondary drive shaft 130 when the bore 138 is at the three o'clock position on the face 129 of the wheel 128. And, a bottom position of the first end of the secondary drive shaft 130 (shown in FIGS. 6*a-e*) will be discussed as the position of the first end of the secondary drive shaft 130 when the bore 138 is at the six o'clock position on the face 129 of the wheel 128. And, a left position of the first end of the secondary drive shaft 130 (shown in FIGS. 7*a-e*) will be discussed as the position of the first end of the secondary drive shaft 130 when the bore 138 is at the nine o'clock position on the face 129 of the wheel 128.

As the secondary drive shaft 130 moves through its possible positions on the circular path, the head adapter 110 (and in this embodiment the ball 300 as well, inasmuch as they are fixed to one another in the described concentric configuration) is caused to rock forward and backward in a tilt plane, that is parallel to the Y-Z plane, about the center of rotation 301 of the ball 300, and simultaneously to rotate about the longitudinal axis of the stem 112, which is aligned with the center of rotation 301. More particularly, as shown in FIGS. 4*a-e*, when the first end of the secondary drive shaft 130 is in the top position, the head adapter 110 is at a backwardmost position, in which the stem 112 is tilted to its farthest point away from the wheel 128 in the tilt plane (e.g., tilted approximately 10 degrees backward, with respect to the Z direction, in the tilt plane). As the first end of the secondary drive shaft 130 moves from the top position to the right position, the head adapter 110 tilts forward and begins rotating clockwise about the longitudinal axis of the stem 112 (when viewing the longitudinal axis of the stem 112 toward the ball 300). As shown in FIGS. 5*a-e*, when the first end of the secondary drive shaft 130 reaches the right position, the head adapter 110 is approximately vertical (parallel to the Z direction), but rotated clockwise about the longitudinal axis of the stem 112 through half of the rotation angle that it will ultimately sweep (e.g., the head adapter 110 is rotated at approximately 10 degrees clockwise from its original rotational orientation). As the first end of the secondary drive shaft 130 moves from the right position to the bottom position, the head adapter 110 tilts farther forward and begins rotating counterclockwise about the longitudinal axis of the stem 112 (when viewing the longitudinal axis of the stem 112 toward the ball 300). As shown in FIGS. 6*a-e*, when the first end of the secondary drive shaft 130 reaches the bottom position, the head adapter 110 is at a forwardmost position, in which the stem 112 is tilted to its farthest point toward the wheel 128 in the tilt plane (e.g., tilted approximately 10 degrees forward, with respect to the Z direction, in the tilt plane), and has returned to the rotational orientation it occupied at the backwardmost position. As the first end of the secondary drive shaft 130 moves from the bottom position to the left position, the head adapter 110 begins tilting backward and continues rotating counterclockwise about the longitudinal axis of the stem 112 (when viewing the longitudinal axis of the stem 112 toward the ball 300). As shown in FIGS. 7*a-e*, when the first end of the secondary drive shaft 130 reaches the left position, the head adapter 110 is again approximately vertical (parallel to the Z direction), but rotated counterclockwise about the longitudinal axis of the stem 112 through half of the rotation angle that it ultimately sweeps (e.g., the head adapter 110 is rotated at approximately 10 degrees counterclockwise from its original rotational orientation). As the first end of the secondary drive shaft 130 moves from the left position to the top position, the head adapter 110 tilts farther backward and begins rotating clockwise about the longitudinal axis of the stem 112 (when viewing the longitudinal axis of the stem 112 toward the ball 300). As shown in FIGS. 4a-e, when the first end of the secondary drive shaft 130 reaches the top position, the head adapter 110 has returned to the backwardmost position and has returned to the rotational orientation it occupied at the backwardmost position. Accordingly, in the illustrated embodiment, in which the longitudinal axis of the secondary drive shaft 130 is angled approximately 10 degrees with respect to the rotation axis of the wheel 128 (also in this embodiment the longitudinal axis of the primary drive shaft 126), the stem 112 has swept through approximately 20 degrees of tilt angulation about the center of rotation 301 (approximately 10 degrees backward and 10 degrees forward), and the head adapter 110 has twice rotated about the longitudinal axis of the stem 112 approximately 20 degrees (10 degrees clockwise, then 20 degrees counterclockwise, and then 10 degrees clockwise again). It should be understood that manipulations of the head adapter (e.g., 110) effect the same manipulations on the second component (e.g., the ball 300) when they are fixed to one another in this concentric configuration. Thus, in the illustrated embodiment, in which the longitudinal axis of the secondary drive shaft 130 is angled approximately 10 degrees with respect to the rotation axis of the wheel 128 (also in this embodiment the longitudinal axis of the primary drive shaft 126), the ball 300 has swept through approximately 20 degrees of tilt angulation in the tilt plane about the center of rotation 301 (approximately 10 degrees backward and 10 degrees forward), and the ball 300 has twice rotated, about a longitudinal axis of the ball 300 that is collinear with the longitudinal axis of the stem 112, approximately 20 degrees (10 degrees clockwise, then 20 degrees counterclockwise, and then 10 degrees clockwise again).

The structure and/or components of the secondary drive shaft 130, and/or the coupling of the first end of the secondary drive shaft 130 to the wheel 128, preferably allow the secondary drive shaft 130 to rotate about a longitudinal axis of the secondary drive shaft 130 and also translate along its longitudinal axis with respect to the wheel 128. This allows the testing machine to compensate for the center of rotation (of the test device) being located out of alignment with the longitudinal axis of the primary drive shaft. More particularly, as the testing machine operates as described above, the effective length of the secondary drive shaft 130 (the length between the wheel 128 and the head adapter 110) changes as the wheel 128 rotates because the head adapter 110 tilts closer to and farther away from the wheel 128 during operation of the testing machine, and thus the second end of the secondary drive shaft 130 also moves closer to and farther away from the wheel 128 during operation of the testing machine 100. Also as the testing machine 100 operates as described above, the secondary drive shaft 130 must be allowed to rotate about its longitudinal axis with respect to the wheel 128, so that the head adapter 110, as it is being manipulated by the secondary drive shaft 130, does not tilt so far that the ball 300 is removed from the pocket 202 of the baseplate 202.

Accordingly, preferably, the coupling of the first end of the secondary drive shaft 130 to the wheel 128 includes the bearing 140 in the bore 138 near the perimeter of the wheel 128, which bearing 140 permits linear translation of the secondary drive shaft 130 within the bore 138 (i.e., along the longitudinal axis of the secondary drive shaft 130) and rotation of the secondary drive shaft 130 (about the longitudinal axis of the secondary drive shaft 130) with respect to the bore 138. The bearing 140 thus maintains the first end of the secondary drive shaft 130 within the bore 138 while permitting the first end of the secondary drive shaft 130 to move as necessary during the operation of the testing machine 100 as described above. Suitable bearings include, but are not limited to, a Combination Linear and Rotary Motion Fixed-Alignment Bearing, available from McMaster-Carr Supply Company (http://www.mcmaster.com), as catalog numbers 6485K12, 6485K14, 6485K15 and 6485K17, or from another parts supply company.

In some embodiments of the present invention, the first end of the secondary drive shaft 130 is fixed to the outer region of the wheel 128, and the second end of the secondary drive shaft 130 is fixed to the cap 114 of the head adapter 110, and the secondary drive shaft 130 includes an angle joint (not shown) that accommodates the angular offset of the secondary drive shaft 130 relative to the primary drive shaft 126, and the secondary drive shaft 130 further includes a coupling (not shown) that connects two portions of the secondary drive shaft 130, which coupling enables the portions to contract toward one another and expand away from one another, as necessary for adjustment of the effective length of the secondary drive shaft 130 during operation of the testing machine 100, and further enables the portions to rotate relative to one another about their longitudinal axes, as necessary to prevent the aforementioned removal of the ball 300 from the pocket 202 of the baseplate 200 (due to an overtilting of the head adapter 110) during operation of the testing machine 100. Such couplings are known in the art and available, e.g., from the McMaster-Carr Supply Company (http://www.mcmaster.com) or another parts supply company. It should be understood that the secondary drive shaft 130 can be made length-adjustable (or longitudinally translatable) and longitudinally rotationally free relative to the wheel 128 through other configurations and part combinations without departing from the scope of the present invention.

While the articulation pattern of the ball 300 has been described as angulation about the center of rotation 301 in a tilt plane parallel to the Y-Z plane during rotation about a longitudinal axis of the ball 300 that remains in the tilt plane (as that longitudinal axis angulates in the tilt plane with the ball 300 during the angulation of the ball 300), it should be understood that the angulation of the articulation can alternatively be described as being in two planes that are, for example, perpendicular to one another and intersect with one another at a line of intersection that extends in the Z direction and is perpendicular to the axis of rotation of the wheel 128. Therefore, the articulation pattern would include angulation about the center of rotation (e.g., 301) in a first plane (e.g., a first of those planes), during angulation about the center of rotation (e.g., 301) in a second plane (e.g., a second of those planes), during rotation about a longitudinal axis of the second component (e.g., the ball 300) that remains in a third plane that intersects the first and second planes at a line of intersection that is perpendicular to the axis of rotation of the wheel 128 (e.g., in this embodiment the third plane is the above described tilt plane that is parallel to the Y-Z plane and includes the axis of rotation of the wheel 128). Stated alternatively, for example, if the first and second planes are perpendicular to one another and disposed at respective convergent angles to the third plane, the angulation about the center of rotation in the first plane sweeps an angulation angle that is twice the angular offset (of the longitudinal axis of the second drive shaft 130 relative to the rotation axis of the wheel 128) multiplied by the cosine of the convergent angle between the first plane and the third plane, and the angulation about the center of rotation in the second plane sweeps an angulation angle that is twice the angular offset (of the longitudinal axis of the second drive shaft 130 relative to the rotation axis of the wheel 128) multiplied by the sine of the convergent angle between the first plane and the third plane. The rotation about the longitudinal axis of the second component (e.g., the ball) still sweeps a rotation angle that is approximately double the angular offset of the longitudinal axis of the second drive shaft 130 relative to the axis of rotation of the wheel 128. Accordingly, it is understood that by varying the angular offset (e.g., of the longitudinal axis of the second drive shaft 130 relative to the rotation axis of the wheel 128), and by varying the convergent angles of the first and second reference planes (e.g., reorienting the stationary component of the test device or otherwise adjusting the planes of interest relative to the rotation axis of the wheel 128), many desired articulation movements, in a number of orientations and with a number of sweep ranges, can be achieved and/or measured using the present invention. (It should be understood that embodiments where these and other parameters of the apparatus are adjustable to enable a variety of uses for a given testing machine, are also contemplated by the present invention.) In the illustrated embodiment, for example, if it is desirable to test the articulation of the joint in two planes to, e.g., more than 14 degrees in each plane, the angular offset of the axis of rotation of the wheel 128 and the longitudinal axis of the second drive shaft 130 can be set at 10 degrees, and the two planes can be referenced as perpendicular to one another and each at 45 degrees relative to the rotation axis of the wheel 128, in which case the ball 300 would be known by the above described mathematical relationship to articulate in one of those two planes a total of 2*10*cos(45)=14.142 degrees, and the other of those two planes at a total of 2*10*sin(45)=14.142 degrees (which happen to be the same in this case due to the equivalence of the 45 degree convergent angles). This setup is illustrated in the figures, which show the lower baseplate 200 being disposed at a 45 degree angle relative to the rotation axis of the wheel 128. As another example, if the planes are set at 30 degrees and 60 degrees, respectively, relative to the rotation axis of the wheel 128, and the angular offset of the longitudinal axis of the second drive shaft 130 is 15 degrees relative to the axis of rotation of the wheel 128, then the ball 300 would be known by the above described mathematical relationship to articulate in one of those two planes a total of 2*15*cos(30)=25.981 degrees, and the other of those two planes at a total of 2*15*sin(30)=15 degrees. It should be understood that these examples of alternate geometric frameworks are provided to illustrate the utility of the invention to enable measurement of the joint performance, and/or ensure sufficient angulation and/or rotation of the joint components, in multiple planes and axes using appropriate mathematical equations to quantify the relationship of the angulations and rotations relative to the rotation axis of the wheel 128 and the other geometric reference points discussed, and that other geometric frameworks can be referenced as necessary to achieve desired performance, measurements, or evaluations. For example, reference planes that are not perpendicular to one another or to the rotation axis of the wheel 128 are also contemplated, as well as multiple planes that are in various orientations relative to one another and to the rotation axis of the wheel 128.

Also, in some embodiments of the present invention, the motion of the head adapter 110 can be controlled by placing motion control structures (e.g., panels, flanges, protuberances, or the like, adjacent (and/or attached to) the head adapter 110 or another part of the testing apparatus 100. For example, two panels can be disposed in parallel to one another and parallel to the Y-Z plane direction, on either side of the head adapter 110 (i.e., spaced apart from one another in the X direction). They can be disposed on either side of the head adapter 110 to interfere with the movement of the head adapter 110 caused by the operation of the motor 124, which interference causes the head adapter 110 to move in the desired manner, or prevent the head adapter 110 from moving in an undesirable manner.

Figure 8B:
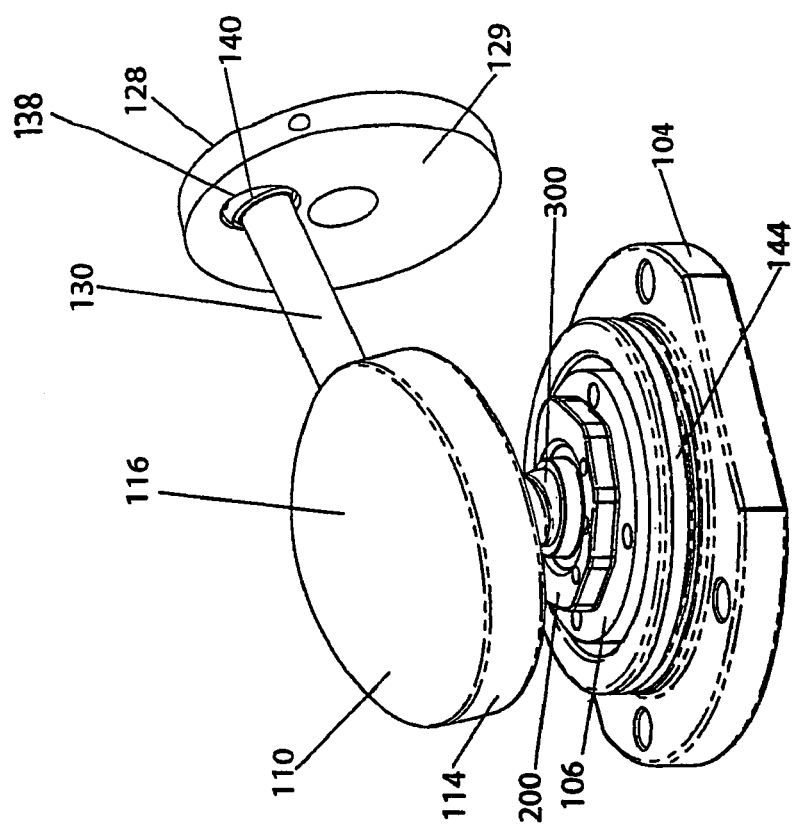
FIGS. 8a-b show a tank and an o-ring of the present invention in use with the testing apparatus of FIGS. 1a-d.
Figure 8A:
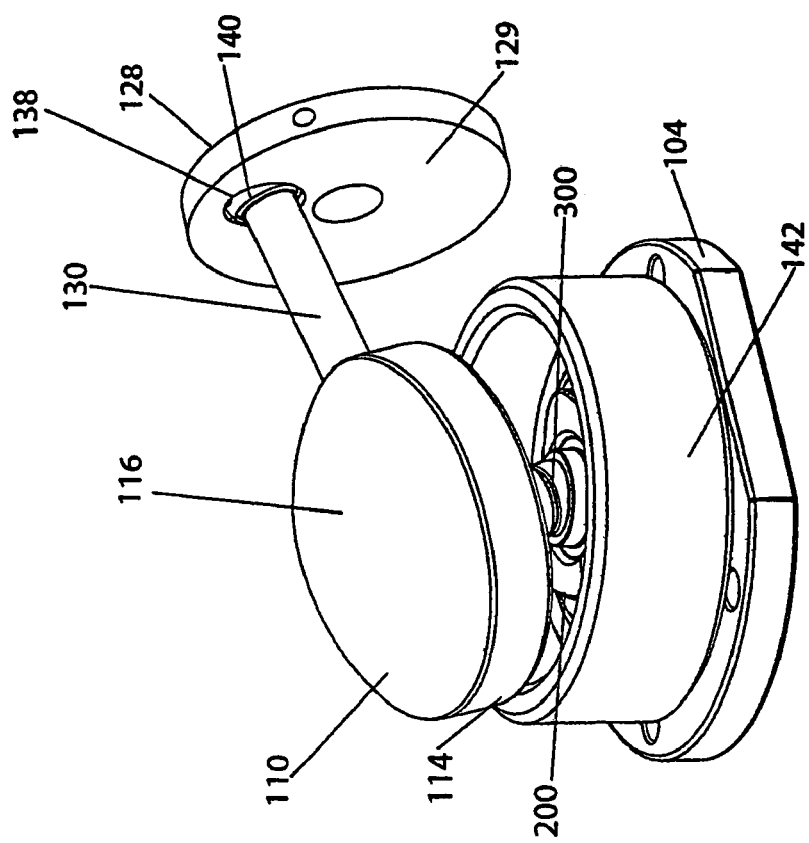

For some uses of the testing apparatus of the present invention, it may be desirable to submerge the test device in a liquid so that any wear debris generated as a result of the articulation of the components of the test device during the testing procedure can be captured and later analyzed. Embodiments of the testing apparatus of the present invention for use in these cases (and others) include additional elements useful to help accomplish this. While any suitable additional elements in this regard are contemplated by the present invention, FIGS. 8a-b illustrate two examples of such components adapted for use with the testing apparatus 100 illustrated in FIGS. 1a-e. More particularly, FIG. 8a shows certain elements of the testing apparatus 100 (each identified by its respective reference number), as well as a cylindrical tank 142 mounted on the support block 104 and surrounding the testing block 106 to a height greater than the height of the components (plate 200 and ball 300) of the test device (other tanks or other structures of other shapes, sizes and configurations can alternatively or additionally be used without departing from the scope of the present invention), so that the components can be completely submerged in the debris-capturing substance. A seal is provided between the cylindrical tank 142 and the block 104 by a rubber o-ring 144 (other suitable elements for providing a seal between the tank 142 and the support bock 104 against the debris-capturing substance in the tank 142 can alternatively or additionally be used without departing from the scope of the present invention). This is illustrated in FIG. 8b (which shows the same configuration but without the tank 142 so that the o-ring 144 can be viewed). Accordingly, debris from the test device can be captured in a substance (not shown) in the tank 142, and later removed from the tank 142 for analysis. One or more holes (not shown) in the tank 142 can be provided for introduction or removal of the capturing substance, in conjunction with appropriate hoses and pumps, in manners known in the art.

Inasmuch as simple rotation of the wheel 128 in the illustrated embodiment effects the desired articulation (with the simple adjustment of the angular offset (of the longitudinal axis of the second drive shaft 130) effect the desired angles for angulation and rotation), and the loading is distinct from the drive assembly, the present invention is shown to be simple in function, and easily adjustable to a variety of uses for testing not only spinal joints, but also hip, knee, and other joints.

While there have been described and illustrated specific embodiments of instrumentation, it will be apparent to those skilled in the art that variations and modifications are possible without deviating from the broad spirit and principle of the invention. The invention, therefore, shall not be limited to the specific embodiments discussed herein.

The invention claimed is:

1. A testing apparatus for an articulating implant comprising:
    a support structure for engaging a part of the implant;
    an adapter for engaging a testing block, wherein the testing block undergoes positionally equivalent or positionally non-equivalent articulations as compared to articulations of the adaptor, and the testing block undergoes angularly equivalent or angularly non-equivalent articulations as compared to articulations of the adaptor;
    a load assembly coupled with the adapter and having an air compressor for applying a load onto the adapter; and
    a drive assembly coupled with the adapter, wherein operation of the drive assembly causes angulation and rotation of the adapter relative to the support structure, which in turn causes angulation and rotation of the testing block and part of the implant relative to one another.

2. The apparatus of claim 1, wherein the articulating implant is selected from a group consisting of an intervertebral disc joint, an artificial intervertebral disc joint, a hip joint and a knee joint.

3. The apparatus of claim 1, wherein the drive assembly comprises a first drive shaft having a first end connected with a center of a rotatable wheel, the first drive shaft being rotatable about a longitudinal axis thereof for causing rotation of the wheel.

4. The apparatus of claim 3, wherein the drive assembly further comprises a second drive shaft having a first end connected with an outer region of the wheel and a second end connected to the adapter, the second drive shaft having a longitudinal axis that is at an angle relative to the longitudinal axis of the first drive shaft, wherein rotation of the first shaft about the longitudinal axis thereof causes angulation and rotation of the adapter.

5. The apparatus of claim 1, wherein the adapter has a semispherical surface facing away from the support structure.

6. The apparatus of claim 1, wherein the testing block and the part of the implant are coupled together by opposing articulating surfaces.

7. The apparatus of claim 6, wherein the opposing articulating surfaces comprise a ball and socket joint.

8. The apparatus of claim 4, wherein the longitudinal axis of the first drive shaft is angularly offset from the longitudinal axis of the second drive shaft.

9. The apparatus of claim 1, wherein an exterior surface of the part of the joint has a concave central region and the support structure has a central recess adapted to receive the concave central region.

10. The apparatus of claim 1, wherein an exterior surface the part of the implant has one or more bone engaging projections and the support structure has one or more recesses adapted to receive the one or more bone engaging projections.

11. The apparatus of claim 1, wherein the angulation of the testing block and the part of the implant comprises angulation of the testing block and the part of the implant relative to one another in a first plane and a second plane and rotation of the testing block relative to the part of the implant.

12. The apparatus of claim 11, wherein the first plane and the second plane are perpendicular to one another and intersect one another and a third plane at a line of intersection that is perpendicular to the longitudinal axis of the first drive shaft, such that the first plane is disposed at a convergent angle to the third plane, and wherein the angulation about the center of rotation in the first plane sweeps an angulation angle that is equal to the cosine of the convergent angle multiplied by twice a magnitude of the angular offset relationship, and wherein the rotation about the longitudinal axis of the second part sweeps a rotation angle that is double the magnitude of the angular offset relationship.

13. A testing apparatus for an implant having an articulating joint comprising:
    a support structure;
    a load assembly having an air compressor, the load assembly being spaced from the support structure, wherein at least a part of the implant is positionable between the support structure and the load assembly, and wherein the load assembly is capable of applying load to the part of the implant;
    a testing block coupled to the load assembly and adapted to mate with the part of the implant; and
    a drive assembly coupled with the testing block, wherein operation of the drive assembly causes articulating movement between the testing block and the part of the implant while under a load applied by the load assembly.

14. The apparatus as claimed in claim 13, wherein the drive assembly comprises a rotatable wheel and a drive shaft connected with an outer region of the wheel, the drive shaft having a longitudinal axis that is angularly offset from an axis of rotation of the rotatable wheel, the drive assembly being coupled with the testing block, wherein rotation of the wheel causes articulating movement of the testing block relative to the part of the implant while under a load applied by the load assembly, and wherein the articulating movement follows an articulating pattern determined by the angular offset relationship.

15. The apparatus as claimed in claim 14, wherein a first end of the drive shaft is connected with the outer region of the wheel and a second end of the drive shaft is coupled with the testing block, and wherein rotating the wheel causes the outer region of the wheel to travel in a circular path around the axis of rotation of the wheel.

16. The apparatus as claimed in claim 15, further comprising:
    an adapter connected to the second end of the drive shaft, the adapter having a first surface in contact with the testing block and a second surface facing away from the first surface of the adapter;
    the load assembly being coupled with the adapter for applying a load onto the second surface of the adapter, wherein rotation of the wheel causes articulation of the adapter through the drive shaft, which in turn causes articulation of the testing block relative to the part of the implant, and wherein the adapter and the part of the implant are under load from the load assembly during the rotation of the wheel and
    wherein the testing block undergoes positionally equivalent or positionally non-equivalent articulations as compared to articulations of the adaptor, and the testing block undergoes angularly equivalent or angularly non-equivalent articulations as compared to articulations of the adaptor.

17. The apparatus as claimed in claim 16, wherein the second surface of the adapter comprises a convex surface.

18. The apparatus of claim 13, wherein the articulating movement between the testing block and the part of the implant comprises angulation of the implant relative to the testing block in at least two planes and rotation of the part of the implant relative to the testing block.

* * * * *